United States Patent
Majeed et al.

(10) Patent No.: US 7,202,270 B2
(45) Date of Patent: Apr. 10, 2007

(54) CONVENIENT STABLE NON-HYGROSCOPIC CRYSTALLINE SOLID FORMS OF RACEMIC AND CHIRAL LA-PLUS SALTS: PROCESS FOR THEIR MANUFACTURE AND USES

(75) Inventors: Muhammed Majeed, Piscataway, NJ (US); Kalyanam Nagabhushanam, North Brunswick, NJ (US)

(73) Assignee: Sami Labs Limited, Bangalore (IN)

( * ) Notice: Subject to any disclaimer, the term of this patent is extended or adjusted under 35 U.S.C. 154(b) by 422 days.

(21) Appl. No.: 10/710,053

(22) Filed: Jun. 15, 2004

(65) Prior Publication Data

US 2005/0215622 A1 Sep. 29, 2005

Related U.S. Application Data

(60) Provisional application No. 60/320,294, filed on Jun. 20, 2003.

(51) Int. Cl.
*A61K 31/385* (2006.01)
*C07D 339/02* (2006.01)

(52) U.S. Cl. .......................... 514/440; 549/35; 549/39
(58) Field of Classification Search ................ 514/440; 549/35, 39
See application file for complete search history.

(56) References Cited

U.S. PATENT DOCUMENTS

| 6,013,663 | A  | * | 1/2000  | Fujita et al. ................. 514/440 |
| 6,150,358 | A  | * | 11/2000 | Goldstein et al. ......... 514/231.5 |
| 6,204,288 | B1 | * | 3/2001  | Pershadsingh et al. ...... 514/440 |
| 6,313,164 | B1 | * | 11/2001 | Fujita et al. ................. 514/440 |
| 7,030,154 | B2 | * | 4/2006  | Ames ......................... 514/440 |

* cited by examiner

*Primary Examiner*—Deborah C. Lambkin

(57) ABSTRACT

A process for the manufacture of new crystalline salts of N-[2-(dimethylamino)ethyl]-1,2-dithiolane-3-pentanamide (racemic and chiral forms) is described. Such salts are stable, crystalline and have very good solubility in water. The salts exhibit antioxidant properties. They inhibit collagenase and elastase enzymes. They have excellent anti acne activity in addition tyrosinase inhibition. They are, by themselves and in combination with other known agents, important cosmetic ingredients.

4 Claims, No Drawings

CONVENIENT STABLE NON-HYGROSCOPIC CRYSTALLINE SOLID FORMS OF RACEMIC AND CHIRAL LA-PLUS SALTS: PROCESS FOR THEIR MANUFACTURE AND USES

CROSS REFERENCE TO RELATED APPLICATIONS

This application claims the benefit of provisional U.S. Patent application No. 60/320,294 filed on Jun. 20, 2003 the disclosure of which is hereby incorporated by reference.

BACKGROUND OF INVENTION

Alpha Lipoic acid is taken up by cells and is reduced to a pharmacologically active dithiol form in several physiological reactions. However this active dithiol form is effluxed out of the cell rapidly decreasing the effectiveness of α-Lipoic acid.

Various mechanisms have been devised to enhance the retention of the active dithiol form within the cell. One such approach is a structurally modified version of α-Lipoic acid called LA-plus, chemically N-[2-(dimethylamino)ethyl]-1,2-dithiolane-3-pentanamide monohydrochloride, which is represented by the formula

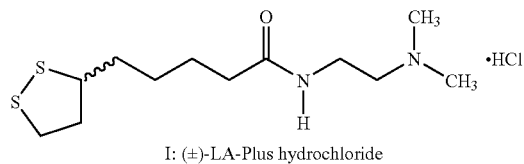

I: (±)-LA-Plus hydrochloride

The protonated form of the corresponding derived dithiol molecule under physiological conditions is more efficiently retained within the cell and performs much better in physiological reactions than the parent α-Lipoic acid. This has been the subject of research papers (Sen, Chandan K; Tirosh, Oren; Roy, Sashwati; Kobayashi, Michael S; Packer, Lester; Biochemical and Biophysical research Communications, (1998), 247, 223–228).

These workers demonstrated that the uptake of LA-Plus was much higher in certain cells and also the intracellular amount of the corresponding dithiol form within the cell was much greater compared to α-Lipoic acid. Hence they came to the conclusion that LA-Plus is an improved form of Lipoic acid with enhanced therapeutic potential.

The (R)-form of LA-Plus described in the above work was synthesized by the reaction of Lipoic acid to which three equivalents of N,N-dimethylethylenediamine were added followed by N-hydroxysuccinimide. Dicylohexylcarbodiimide was subsequently added and the reaction time was one day. The product was extracted into the aqueous phase using hydrochloric acid and extracted into chloroform after basification of the aqueous phase using sodium hydroxide. This organic phase was dried, filtered and evaporated to dryness. The residue was redissolved in dichloromethane and hydrogen chloride gas was passed through the organic solvent up to saturation. The dichloromethane solvent was evaporated and the HCl salt of N,N-dimethyl-N"-2-amidoethyl-lipoate was precipitated using anhydrous ether.

It should be noted that the preparation LA-Plus hydrochloride involves extraction and re-extraction of the product in and out of aqueous/organic media. Also it involves the passage of hydrogen chloride gas, which is corrosive and difficult to use. Several solvents such as chloroform, methylene chloride, and dry diethyl ether are employed in the process.

Hence the synthesis of LA-plus as described in prior art is involved and not easily adaptable to large-scale operations (Sen, Chandan K; Tirosh, Oren; Roy, Sashwati; Kobayashi, Michael S; Packer, Lester; Biochemical and Biophysical research Communications, (1998), 247, 223–228).

More particularly, the product, both the racemeic (±)-LA-Plus hydrochloride and chiral (R)-LA-Plus hydrochloride forms are not good solids. They were also found to be hygroscopic and not easily handled during transfer and other operations.

In spite of the difficulty of handling LA Plus hydrochloride, applications involving this hygroscopic salts have been claimed (U.S. Pat. No. 5,965,618, U.S. Pat. No. 6,090,842, WO 0180851). Hence there is a need for a new salt form of LA-plus base which would be a good solid, non-hygroscopic and easily handled for various operations.

The preparation and use of compositions containing Lipoic acid or its derivatives, including LA-plus, for nutraceutical and cosmetic applications is widely described in prior art for example in U.S. Pat. Nos. 6,743,433 and 6,365,623 that describe compositions for the treatment of acne; U.S. Pat. Nos. 6,387,945, 6,235,772 and 6,090,842 that describe Lipoic acid analogs. The preparations of the current invention were found to be similarly biologically active.

SUMMARY OF INVENTION

The present invention describes a convenient method of manufacture of of LA Plus base (N-[2-(dimethylamino)ethyl]-1,2-dithiolane-3-pentanamide ((±)-N-1-[2-(dimethylamino)ethyl]-5-(1,2-dithiolan-3-yl) pentanamide) from Lipoic acid. In addition stable, crystalline salts of LA Plus are described which are easily stable, non-hygroscopic and handled. Uses of such salts are described in various cosmetic applications such as skin care and hair care applications.

DETAILED DESCRIPTION

Our present invention addresses these issues. In this invention, (±)-Lipoic acid is treated with a slight excess of 1,1'-Carbonyl diimidazole and the intermediate acyl imidazole is reacted with N,N-dimethylethylenediamine to form N-[2-(dimethylamino)ethyl]-1,2-dithiolane-3-pentanamide (LA-Plus base) in methylene chloride solution. Removal of methylene chloride and precipitation of the LA-Plus base as its maleate salt, LA-Plus maleate, forms the rest of the process.

The structures of the materials referred in this patent are shown as follows

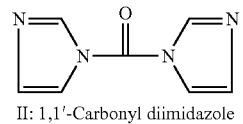

II: 1,1'-Carbonyl diimidazole

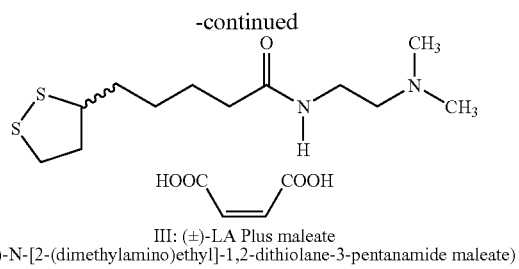

III: (±)-LA Plus maleate
((±)-N-[2-(dimethylamino)ethyl]-1,2-dithiolane-3-pentanamide maleate)

Even though the examples are illustrative of the invention, they do not limit the scope of the invention. Lipoic acid is reacted with carbonyl diimidazole in a solvent such as methylene chloride. It is then treated with N,N-dimethyl-ethylene diamine in the same solvent. The solvent was removed, replaced by acetone and the acid component was added to precipitate the desired material. For example, a similar process can be conceived for N,N-Dimethyl propylene diamine replacing N,N-dimethyl ethylenediamine to give another analog of LA-Plus. Similarly, another reactive acyl imidazole could be formed with 1,1"-Carbonylbis(2-methylimidazole), CAS registry no. 13551-83-2, with similar results. Such variations also fall within the scope of this invention.

We also found that stable, non-hygroscopic salts of LA Plus could be formed with fumaric acid in place of maleic acid as another example illustrating this invention.

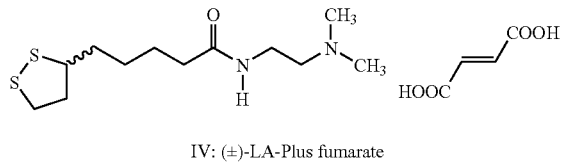

IV: (±)-LA-Plus fumarate

The method is applicable for (±)LAPlus maleate as well as its chiral forms. For example, instead of (±)-Lipoic acid, if one uses R-(+)-Lipoic acid as the starting material, one again obtains the corresponding R-(+)-LA Plus maleate or fumarate depending on the acid that is employed for salt formation.

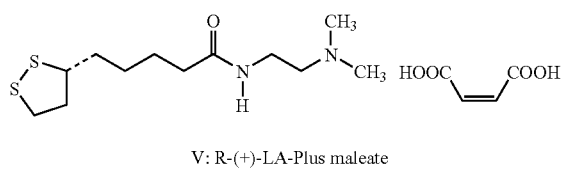

V: R-(+)-LA-Plus maleate

The solubility data on the LA Plus salts described in this patent are given in Table 1

TABLE 1

| | Solubility Data | | |
|---|---|---|---|
| SAMPLE | WATER (D. D.) | ETHANOL (95%) | PROPYLENE GLYCOL |
| Alpha lipoic acid | 0.03% | 57% | 20% |
| LA plus (Maleate) | 60% | 7.35% | 13% |
| LA plus (Fumarate) | 100% | 51% | 23% |

TABLE 1-continued

| | Solubility Data | | |
|---|---|---|---|
| SAMPLE | WATER (D. D.) | ETHANOL (95%) | PROPYLENE GLYCOL |
| R (+)-LA plus (Maleate) | 60% | 6.84% | 10% |

Results in gm/dl; tests were done at 35 to 40° C. temperature.

It is clear from the data that the solubilities of the maleate and fumarate salts in water are much higher than that of α-Lipoic acid. Hence these stable, nonhygroscopic salts are easy to formulate in water based formulations.

TABLE 2

Antioxidant assay by DPPH radical scavenging activity

| | Absence of sun light | | Exposure to sun light for 5 minutes | |
|---|---|---|---|---|
| Sample/Batch No. | Conc. | % Scavenging | Conc. | % Scavenging |
| Alpha lipoic acid | 6 mg | 50% | 45 μg | 50% |
| LA plus (Maleate) | 6.6 mg | 54% | 55 μg | 53% |
| R(+)-LA plus (Maleate) | 6.6 mg | 49% | 55 μg | 47% |
| LA plus (Fumarate) | 6.2 mg | 57% | 55 μg | 50% |
| Ascorbic acid | 6 μg | 71% | 6 μg | 59% |

LA Plus maleate and fumarate salts and α-Lipoic acid showed a marked difference in scavenging the DPPH radical when exposed to sunlight which was not shown by Ascorbic acid. Even when the concentration was 120 times lesser, the activity was comparable with exposure to sunlight (5 minutes). This data attest to the unique antioxidant ability of LA Plus salts in particular.

The inhibitory properties of LA Plus salts of the enzyme tyrosinase is shown in Table 3. Tyrosinase inhibition is one of the established in vitro methods of evaluating the skin fairness property.

TABLE 3

Activity on Tyrosinase

| | Tyrosinase | |
|---|---|---|
| Sample | Conc. | % Inhibition |
| Alpha lipoic acid (KU030121) | 100 μg | 51% |
| LA plus (Maleate) | 120 μg | 58% |
| R(+)-LA plus (Maleate) | 120 μg | 58.6% |
| LA plus (Fumarate) | 120 μg | 53% |

LA Plus maleate, LA Plus fumarate and R(+)LA Plus maleate (the three water soluble LA Plus salts) and α-Lipoic acid have thus the property as skin fairness/de-pigmentation product.

The inhibitory studies of LA Plus maleate, LA Plus fumarate and R(+) LA Plus maleate (the three water soluble LA Plus salts) and α-Lipoic acid on Collagenase and Elastase disclosed that these Lipoic acid derived salts are good inhibitors of these enzymes. The $IC_{50}$ values for Collagenase were found to be the same, namely, 1.6 mg/ml for LA Plus maleate, LA Plus fumarate and R(+)LA Plus maleate (the three water soluble LA Plus salts) and α-Lipoic acid. Similarly the $IC_{50}$ values for Elastase were found to be the same, namely, 1.4 mg/ml for LA Plus maleate, LA Plus fumarate and R(+)LA Plus maleate (the three water soluble LA Plus salts) and α-Lipoic acid. The formulations containing these salts are thus useful in antiaging effects and in preventing wrinkle formations in the skin. Our research further disclosed that LA Plus maleate, LA Plus fumarate and R(+)LA Plus maleate (the three water soluble LA Plus salts) and α-Lipoic acid display very good inhibition properties against *Propionibacterium acnes*. The important findings from these studies are as follows.

Two of derivatives of α-Lipoic acid viz., R(+)LA+Maleate and α-LA+Maleate are giving good inhibition of *P. acnes* and are showing inhibition at the minimum concentration of 1.0%. This is well comparable with that of the control [Clindamycin].

The compound α-Lipoic acid and one of its derivatives, α-LA+Fumarate are giving inhibition of *P. acnes* at the concentrations of 5 and 2% respectively.

The inhibitory activity of these compounds are in the following order: R(+)LA Plus Maelate>LA Plus Maleate>LA Plus Fumrate>α-Lipoic acid Our results show that the LA Plus salts show a better activity than a standard drug like Clindamycin.

The results are presented in the following Table 4

TABLE 4

| | Zone of inhibition (in mm) | | | | |
|---|---|---|---|---|---|
| Conc. of the sample (%) | α-Lipoic acid (α- LA) | R(+) LA Plus Maleate | LA Plus Maleate | LA Plus Fumarate | Clindamycin |
| 10 | 8 | 15 | 11 | 10 | 20 |
| 5 | 7 | 12 | 9 | 8 | 15 |
| 2 | 0 | 10 | 8 | 7 | 9 |
| 1 | 0 | 8 | 7 | 0 | 7 |
| 0.5 | 0 | 0 | 0 | 0 | 0 |

Conclusion: From these studies it is evident that two derivatives of α-Lipoic acid, viz., R(+)LA Plus Maleate and LA Plus Maleate can work as good antiacne agents.

ILLUSTRATIVE EXAMPLES

Example 1

(±)-Maleate salt of N-[2-(dimethylamino)ethyl]-1,2-dithiolane-3-pentanamide((±)-Maleate salt of N-1-[2-(dimethylamino)ethyl]-5-(1,2-dithiolan-3-yl)pentanamide, (±)-LA Plus maleate salt)

1,1"-Carbonyl diimidazole (43 g in 150 ml of methylene chloride under nitrogen atmosphere) was cooled to 5–10° C. To the cold solution (±)-Lipoic acid (52 g in 250 ml of methylene chloride) was added slowly. Stirring was continued at room temperature after completion of addition. A clear solution was obtained. This solution was cooled to 5–10° C. and N,N-Dimethylethylenediamine (27 g) was added slowly.

The resultant solution was stirred for 3 hours at room temperature The methylene chloride layer was dried over sodium sulfate and the solvent was removed. The residue was dissolved in dry acetone (250 ml) and to this well-stirred solution, maleic acid (28 g in 250 ml acetone) was added slowly. The precipitated product was filtered and dried.

Yield: 89 g; Mp: 125–127° C.; Elemental analysis (Calculated values for $C_{16}H_{28}N_2O_5S_2$ in parentheses) Carbon, 48.94% (48.96%); Hydrogen, 7.22% (7.19%); Nitrogen, 7.15% (7.14%).

Example 2

R-(+)-Maleate salt of N-[2-(dimethylamino)ethyl]-1,2-dithiolane-3-pentanamide(R-(+)-Maleate salt of N-1-[2-(dimethylamino)ethyl]-5-(1,2-dithiolan-3-yl)pentanamide, (+)-LA Plus maleate salt)

Same procedure as in example 1 excepting that R-(+)-lipoic acid was used in place of (±)-Lipoic acid.

Mp: 125–127° C.; Elemental analysis (Calculated values for $C_{16}H_{28}N_2O_5S_2$ in parentheses): Carbon, 49.12% (48.96%); Hydrogen, 7.06% (7.19%); Nitrogen, 6.99% (7.14%) Specific rotation: 53.80 (c=10.52 mg/ml of water)

Example 3

(±)-Fumarate salt of N-[2-(dimethylamino)ethyl]-1,2-dithiolane-3-pentanamide(±)-Fumarate salt of N-1-[2-(dimethylamino)ethyl]-5-(1,2-dithiolan-3-yl)pentanamide, (±)-LA Plus fumarate salt)

Same procedure as in Example 1 excepting that fumaric acid is used in place of maleic acid Mp: 76–78° C.; Elemental analysis: (Calculated for values $C_{16}H_{28}N_2O_5S_2$ in parentheses) Carbon, 48.87% (48.96%); Hydrogen, 6.99% (7.19%); Nitrogen, 7.22% (7.14%)

The invention claimed is:

1. A process for the manufacture of stable, non-hygroscopic, crystalline salts of the base (±)-N-[2-(dimethylamino)ethyl]-1,2-dithiolane-3-pentanamide((±)-N-1-[2-(dimethylamino)ethyl]-5-(1,2-dithiolan-3-yl)pentanamide, (±)-LA Plus base) which consists of reacting (±)-Lipoic acid with 1,1"-Carbonyl diimidazole followed by the addition of N,N-dimethylethylenediamine and precipitating the product with an acid component.

2. A process as claimed in claim 1 wherein the acid component is chosen from among maleic acid, fumaric acid.

3. A process for the synthesis of stable, non-hygroscopic crystalline salts of R-N-[2-(dimethylamino)ethyl]-1,2-dithiolane-3-pentanamide(R-N-1-[2-(dimethylamino)ethyl]-5-(1,2-dithiolan-3-yl)pentanamide, R-LA Plus base) which consists of reacting R-(±)-Lipoic acid with 1,1"-Carbonyl diimidazole followed by the addition of N,N-dimethylethylenediamine and precipitating the product with an acid component.

4. A process as claimed in claim 3 wherein the acid component is chosen from among maleic acid, fumaric acid.

* * * * *